United States Patent
Grieshaber et al.

(10) Patent No.: US 9,492,319 B2
(45) Date of Patent: Nov. 15, 2016

(54) IMPLANT FOR THE TREATMENT OF GLAUCOMA

(71) Applicant: Grieshaber Ophthalmic Research Foundation, St. Gallen (CH)

(72) Inventors: Hans R. Grieshaber, Schaffhausen (CH); Matthias C. Grieshaber, Binningen (CH); Robert C. Stegmann, Pretoria (ZA)

(73) Assignee: GRIESHABER OPHTHALMIC RESEARCH FOUNDATION, St. Gallen (CH)

( * ) Notice: Subject to any disclaimer, the term of this patent is extended or adjusted under 35 U.S.C. 154(b) by 13 days.

(21) Appl. No.: 13/965,650

(22) Filed: Aug. 13, 2013

(65) Prior Publication Data

US 2013/0331760 A1 Dec. 12, 2013

Related U.S. Application Data

(63) Continuation of application No. PCT/EP2011/052683, filed on Feb. 23, 2011.

(51) Int. Cl.
  *A61M 27/00* (2006.01)
  *A61F 9/00* (2006.01)
  *A61F 9/007* (2006.01)

(52) U.S. Cl.
  CPC .... *A61F 9/00781* (2013.01); *A61F 2210/0014* (2013.01)

(58) Field of Classification Search
  CPC .................. A61F 2/86–2/89; A61F 9/00781; A61F 2210/0014
  See application file for complete search history.

(56) References Cited

U.S. PATENT DOCUMENTS 5,360,398 A 11/1994 Grieshaber
5,360,399 A 11/1994 Stegmann (Continued)

FOREIGN PATENT DOCUMENTS

EP 0898947 3/1999
WO WO2004/026347 4/2004

(Continued)

OTHER PUBLICATIONS

International Search Report issued by the European Patent Office in International Application PCT/EP2011/052683.

*Primary Examiner* — Philip R Wiest
*Assistant Examiner* — Benjamin Klein
(74) *Attorney, Agent, or Firm* — Henry M. Feiereisen LLC; Ursula B. Day

(57) ABSTRACT

The invention refers to a tube configured as an implant for insertion at least at one location into the exposed Schlemm's canal of an eye and which, for example, has been mechanically dilated. The elongated tube insertable into the Schlemm's canal includes a plurality openings that are arranged at the tube in axial direction distanced from each other by ring parts and that are in communication with the trabecular tissue the interior space of the tube and the aqueous humor veins of the episcleral vein system and further includes openings oriented in axial direction at a circular arc shaped segment corresponding to the cross section profile of the tube. To realize the natural trabecular aqueous humor drainage, the tube are inserted into the Schlemm's canal that either the openings in the segment are in communication with the aqueous humor veins or that segment with the openings are associated with the trabecular tissue.

12 Claims, 4 Drawing Sheets

(56) References Cited

U.S. PATENT DOCUMENTS

| | | |
|---|---|---|
| 5,454,783 A | 10/1995 | Grieshaber |
| 5,486,165 A | 1/1996 | Stegmann |
| 5,487,747 A | 1/1996 | Stagmann |
| 5,676,650 A | 10/1997 | Grieshaber |
| 5,693,062 A | 12/1997 | Stegmann |
| 5,716,328 A | 2/1998 | Grieshaber |
| 5,807,401 A | 9/1998 | Grieshaber |
| 6,149,274 A | 11/2000 | Grieshaber |
| 6,332,866 B1 | 12/2001 | Grieshaber |
| 6,375,642 B1 | 4/2002 | Grieshaber |
| 6,561,974 B1 | 5/2003 | Grieshaber |
| 6,666,841 B2 | 12/2003 | Gharib et al. |
| 6,726,676 B2 | 4/2004 | Stegmann |
| 6,764,439 B2 | 7/2004 | Stegmann |
| 8,034,105 B2 | 10/2011 | Stegmann et al. |
| 2002/0013546 A1 | 1/2002 | Grieshaber |
| 2004/0127843 A1 | 7/2004 | Tu et al. |
| 2004/0210181 A1 | 10/2004 | Vass et al. |
| 2005/0192527 A1 | 9/2005 | Gharib et al. |
| 2006/0155300 A1* | 7/2006 | Stamper et al. .............. 606/107 |
| 2007/0088432 A1 | 4/2007 | Solovay et al. |
| 2007/0213810 A1* | 9/2007 | Newhauser et al. ......... 623/1.16 |
| 2008/0228127 A1 | 9/2008 | Burns et al. |
| 2009/0227934 A1* | 9/2009 | Euteneuer et al. ............... 604/8 |
| 2011/0046536 A1 | 2/2011 | Stegmann |
| 2011/0118649 A1 | 2/2011 | Stegmann |
| 2011/0224597 A1 | 9/2011 | Stegmann et al. |
| 2012/0310072 A1 | 12/2012 | Grieshaber |
| 2013/0331760 A1 | 12/2013 | Grieshaber |

FOREIGN PATENT DOCUMENTS

| | | |
|---|---|---|
| WO | WO2005/107664 | 11/2005 |
| WO | WO2008/002377 | 1/2008 |
| WO | WO2008002377 | 1/2008 |
| WO | WO2009/042596 | 4/2009 |
| WO | WO2010/072574 | 7/2010 |

* cited by examiner

IMPLANT FOR THE TREATMENT OF GLAUCOMA

CROSS-REFERENCES TO RELATED APPLICATIONS

This application is a continuation of copending PCT International Application PCT/EP2011/052683 filed Feb. 23, 2011 and published Aug. 12, 2012 as WO 2012/113450 A1 pursuant to 35 U.S.C. 119(a)-(d), the subject matter of which is incorporated herein by reference.

BACKGROUND OF THE INVENTION

The present invention relates to an implant for the treatment of glaucoma, comprising an elongated tube insertable into the Schlemm's canal exposed at least at one location of the sclera, the tube is configured flexible and bendable and includes a plurality of openings arranged in axial and circumferential direction in the tube wall at a distance from each other for the trabecular drainage of the aqueous humor, which openings connect with the trabecular tissue, the interior space of the tube and the episcleral venous system.
Ophthalmological Background In a healthy eye, the drainage of the circulating aqueous humor (humor aquosus) occurs from the posterior chamber to the anterior chamber and lets off in the chamber angle (angulus iridocornealis) via the trabelular tissue into the Schlemm's canal and from there, via the episcleral venous system moved into the circulatory blood stream. In pathological conditions of the eye, in particular, when resistance to the flow occurs, for example, due to a Schlemm's canal that is clogged by conglutination or similar condition, a continuous drainage of the aquous humor formed by the epithelium of the ciliary body and continually renewed, is not sufficient or no longer realized. As a result, the intraocular pressure (IOP) increases to a degree, that the circulation of the visual nerve and thus its function becomes diminished. This functional deficiency can lead to disease known as glaucoma or "grüner star" and can lead to blindness in one or both eyes.

PRIOR ART

Methods of treatment for glaucoma and maintenance of drainage of the anatomically natural aqueous humor are known, as well as various devices, each of which comprise an implant that is inset table into the circular Schlemm's canal that has been surgically exposed, each of which includes an elongated flexible tube and including several openings arranged in axial direction and at a distance from each other that are connected to the interior space of the tube (cf. EP 0 898 947 Grieshaber; WO 2010/072574 Stegmann et al.; WO 2009/042596 Schieber et al.).

Furthermore, to maintain the aqueous humor drainage, a device for insertion into the circular Schlemm's canal is known which, for the radial support of the lumen, includes several support elements arranged distanced and connected relative to each other for the radial support of the lumen, which elements are for example, ball shaped or such (cf. U.S. Pat. No. 8,034,105 Stegmann et al. WO 2008/002377 Badawi).

With other devices for treatment of glaucoma, the aqueous humor is artificially drained by means of a tube-shaped branched element (shunt) by rerouting it from the anterior chamber into the Schlemm's canal and from there via the episcleral venous system into the blood circulation of the eye (cf. U.S. 2007/0088432 Solovay et al.; U.S. 2005/0192527 and U.S. Pat. No. 6,666,841 Gharib et al.; U.S. 2004/0210181 Vass et al.; U.S. 2004/0127843 Tu et al.).

In other methods as well as devices for treating glaucoma, the aqueous humor is rerouted, for example through a surgical bypass between the anterior chamber and a suitable vein of the episcleral venous system or, from the anterior chamber into a surgically provided choroidal space between the sclera and the ciliary body, or through a tissue channel which connects the choroidal space with Schlemm's canal. (cf. WO 2004/026347 Stamper et al.; U.S. 2008/0228127 Burns et al.; WO 2005/107664 Conston et al.).

It would therefore be desirable and advantageous to provide an improved implant to obviate prior art shortcomings and to

SUMMARY OF THE INVENTION

According to one aspect of the present invention, a tube-shaped implant is provided which is insertable into the Schlemm's canal, by means of which an interior eye pressure controlling circulation of the aqueous humor via the lumen of the circular Schlemm's canal is realized and thus, the natural trans-trabecular drainage of the aqueous humor into the episcleral venous system and the blood circulation of the eye is improved and permanently maintained.

The implant according to the present invention is characterized in that the tube includes a segment with a circular arc profile cross section, which is provided in axial direction with openings arranged distanced from each other and openings disposed as a geometric pattern in the tube wall, wherein any of the openings are in communication with the hollow cylindrical interior space of the tube extending in axial direction.

In a preferred embodiment of the implant, all burrs, frays and such which occur through laser treatment at the surface and the edges, are eliminated, for example through thermal repair and the edges left from the laser treatment are smoothed with suitable means.

The tube that is inserted into the lumen of the Schlemm's canal (FIG. 3) has the advantage that the Schlemm's canal, on the one hand is kept permanently open and is thus stabilized, and on the other hand that natural trabecular drainage of the aquous humor drains from the trabecular tissue through the dispersed openings into the interior space of the implant and from there through the openings of the segment part into the naturally distributed canaliculi of the episcleral venous system and from there into the circulatory blood stream.

In a variant, tube is inserted into the Schlemm's canal rotated around its longitudinal axis by about 180°, such that the natural trabecular drainage of the aqueous humor drains from the trabecular tissue first through the respective openings in the segment of the tube and from there through the openings distributed at the tube wall into the natural canaliculi of the episcleral venous system and from there into the circulatory blood stream.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
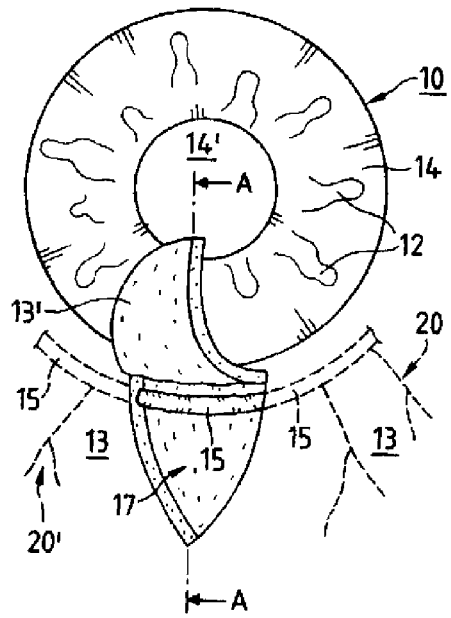
FIG. 1 is a schematic view of the eye with a lamellar cut and an opened scleral flap showing the exposed Schlemm's canal for insertion of a tube configured as an implant according to the present invention.

Throughout all the Figures, same or corresponding elements are generally indicated by same reference numerals.

Figure 2:
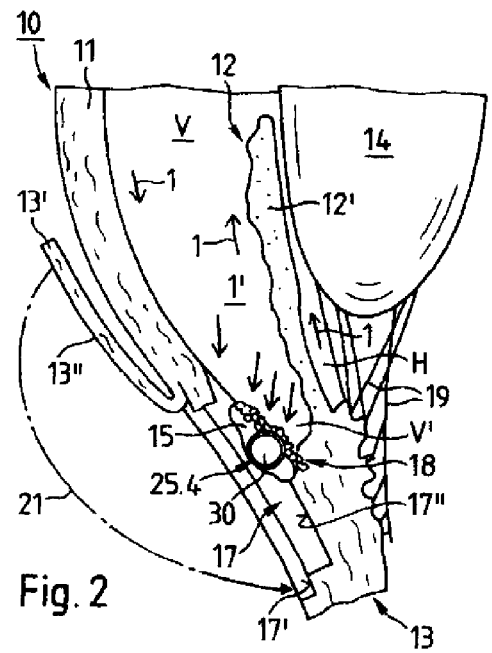
FIG. 2 is a section of the eye shown enlarged and according to line A-A of the implant disposed in the Schlemm's canal.
Figure 3:
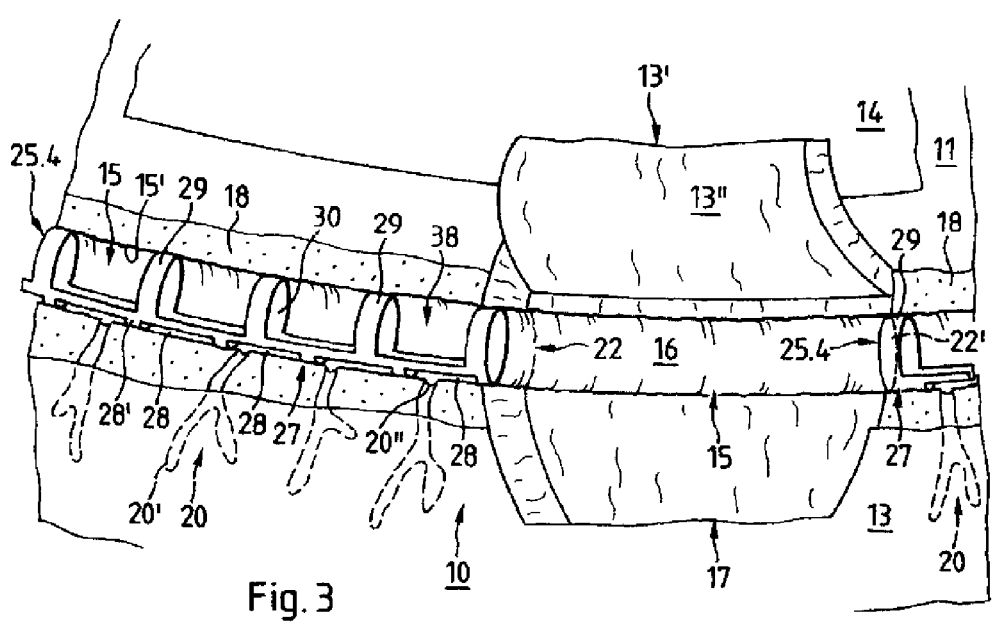
FIG. 3 is a section of the eye shown enlarged and according to a first variant of an implant inserted into the exposed Schlemm's canal.

Turning now to the drawing, and in particular, to FIGS. 1 to 3, for a better understanding of the problem in connection with the glaucoma surgery, each show a section of the eye, wherein FIG. 2 and FIG. 3 each illustrate an implant configured as an elongated tube inserted into the Schlemm's canal by means not shown here.

FIG. 1 shows in a schematic front view an entire eye designated 10 with the lens 14 and the pupil 14', the iris 12, the sclera 13, the partially shown Schlemm's canal 15 and the aqueous humor veins 20 (collector channels) with each of the canaliculi 20'.

Through microsurgery, as depicted in FIG. 1 and in a known manner, a lamellar cut is made in the sclera and after removing a section not shown here in detail, the outer section 13' is flipped open and held in place by means not shown here in detail. The lamellar cut, in the area of the exposed Schlemm's canal 15, forms a scleral bed 17 which after insertion and deposit of the tube-shaped implant is closed up again.

FIG. 2 shows the enlarged section 10 of the eye according to line A-A in FIG. 1, showing the cornea 11, one section 12' of the iris 12, the sclera 13 with the flipped open scleral flap 13', the lens 14, the zonula fibers 19, the posterior chamber H and the anterior chamber V with the iridocorneal angle V' as well as the trabecular tissue 18 preceding the Schlemm's canal 15. The Schlemm's canal 15 oriented circularly around the lens 14, as schematically illustrated in FIG. 2 has a profile cross section of an elongated oval, which starting from one end in the area of the iridocorneal angle V' in the direction of the other oppositely located end, can have a tapered shape.

As further shown in FIG. 2, the tube inserted into the Schlemm's canal 15, as well as the scleral bed 17 with the inner surface 17" and the support surface 17' for the scleral flap 13' to be folded downward in direction 21, which is placed flat with its inner surface 13" at the flat area 17' of the scleral bed 17 and fixed by means not shown here in detail. FIG. 2 shows an embodiment where the tube 25.4 configured as an implant with an interior space 30. Further shown in FIG. 2 is the circulation of the aqueous humor from the anterior chamber H in the direction of the anterior chamber V and designated with arrows 1. According to arrows 1', the aqueous humor reaches through a natural path from the iridocorneal angle V' trough the trabecular tissue 18 into the Schlemm's canal 15 and from there into the venous system and into the circulatory blood stream.

Figure 3A:
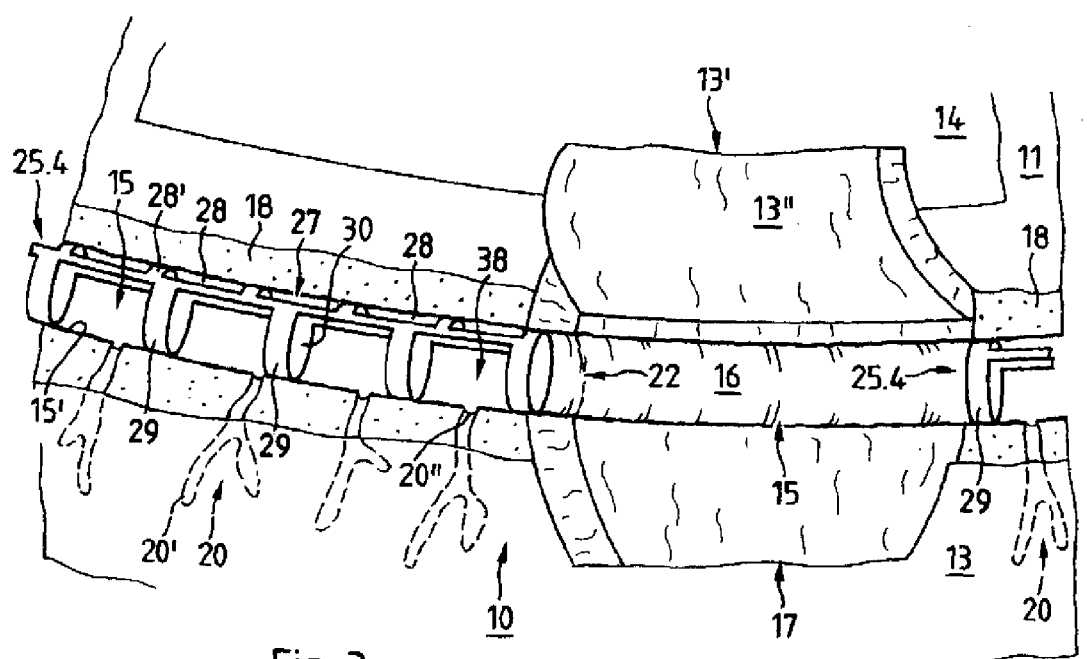
FIG. 3a is the section of an eye according to FIG. 3 with the second variant of an implant inserted into the exposed Schlemm's canal.

FIG. 3 and FIG. 3a each show an enlarged partial section of the eye 10 with the scleral bed 17 and the pulled up scleral flap 13' as well as the tube 25.4, which, for example, has been inserted into the lumen 16 of the circular Schlemm's canal 15, through an exposed opening 22. The tube 25.4 configured as an implant described further below in connection with FIG. 8 is provided with segment 27 extending in axial direction at which a plurality of ring parts 29, configured essentially in circular arc form, are arranged in axial direction and distanced from each other by gaps 38.

The flexibly configured implant inserted into Schlemm's canal 15, as illustrated in FIGS. 3 and 3a has a length extending in circumferential direction of the Schlemm's canal from the first opening 22 to the second opening 22' located opposite of the first opening 22 and is self-adjusting to the natural shape of the Schlemm's canal 15.

As shown in FIG. 3, in the first variant, the tube 25.4 is inserted into the Schlemm's canal 15 and disposed therein in such a manner that each of the ring parts 29 is facing the trabecular tissue 18 and lying against the interior wall 15' of the Schlemm's canal 15, whereby in this Figure, the openings 28 of segment 27 are in communication with the canaliculi 20 and openings 20'' associated with the schematically shown aqueous humor veins 20 (collector channels).

Figure 4:
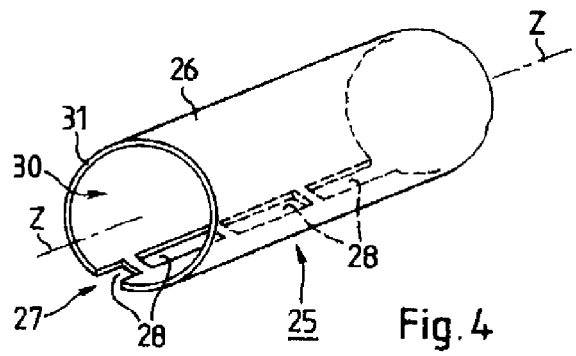
FIG. 4 is a perspective view of a tube shaped preform showing a hollow cylindrical casing with a wall and an interior space, a segment oriented in axial direction as well as an axially oriented axis Z extending through the interior space and showing openings arranged in the axially extending segment of the tube.
Figure 8:
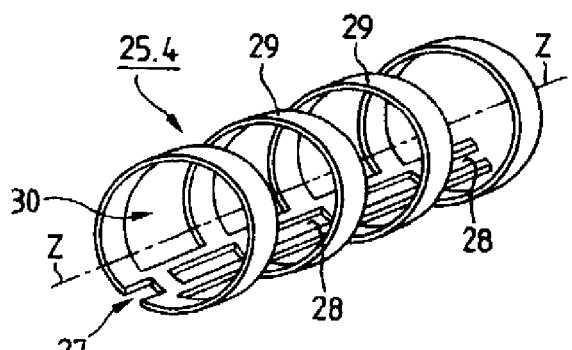
FIG. 8 is a tube shown in perspective view with according to a fourth geometric pattern showing the gaps between each of the ring parts and the additional openings extending in axial direction in the segment.

In the second variant in FIG. 3a, the tube 25.4 is inserted rotated around the longitudinal axis Z as seen in FIGS. 4 and 8 into the Schlemm's canal 15 and placed in a manner so that each of the ring parts 29 that are distanced from each other are adjoining the interior wall 15' of the Schlemm's canal 15 while the gaps 38 between the ring parts 29 are in communication with the canaliculi 20' of the aqueous humor veins 20 and the additional openings in segment part 27 oriented in axial direction at the tube 25.4 and abutting the oppositely located interior wall 15' of the Schlemm's canal 15 are in communication with the trabecular tissue 18.

At this point it should be noted that that the tube 25.4 which is configured as an implant is, for example, dependent on the organic and anatomical state of the Schlemm's canal 15 when inserted into the lumen 16 of the Schlemm's canal 15; as a result, the natural trans-trabecular drainage of the aqueous humor into the episcleral venous system and into the circulatory blood stream is improved and permanently maintained.

To optimize the trans-trabecular aqueous drainage, the Schlemm's canal can be circumferentially dilated by mechanical means for subsequent insertion of the implant of the present invention into the expanded lumen and, for example, deposited at the target location.

FIG. 4 shows a perspective view of the preform 25 of an implant for purposes of illustrating the variously configured implants. Preform 25 consists of a hollow cylindrical casing 26 with a wall 31 and an interior space 30, a segment 27 oriented in axial direction as well as an axially oriented axis Z extending through the interior space. The segment 27 oriented in longitudinal direction has a cross section of a circular arc profile corresponding to the preform 25 and is provided with several openings 28 arranged in axial direction and distanced to each other.

The following describes each of the implants configured from the tube-shaped preforms 25 that are provided with openings 32, 33, 36, 36' and gaps 38 and provided with several openings 28 arranged at the segment 27 and implants from tubes 25.1 to 25.5. The openings 32, 33, 36, 36' and gaps 38 are arranged according to a geometric pattern or a geometric structure in the wall 31 of any of tubes 25.1 to 25.5. The openings 28 are arranged between the webs 28' and oriented in axial direction along axis Z in the segment 27 of each of tubes 25.1 to 25. 5 and distanced from each other so that each opening 20" of the aqueous humor veins (collector channels) is unobstructed for drainage of the aqueous humor through the openings 28. The openings 28 arranged between the webs 28' are, for example, configured as rectangular elongated openings 28 and are of equal size, or are of different sizes.

Figure 5:
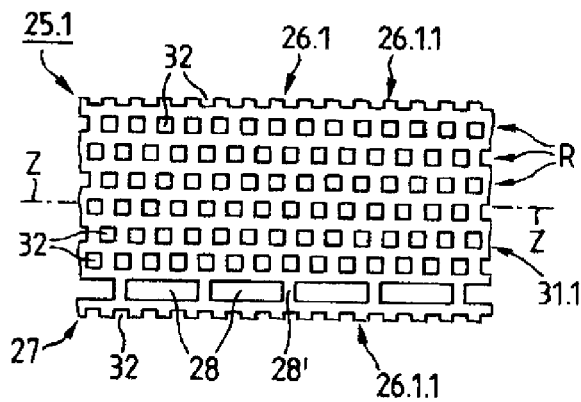
FIG. 5 is a plan view of the tube wall with openings in a first geometric pattern as well as showing additional openings.

FIG. 5 shows in a top view a first embodiment of the tube 25.1 with the casing 26.1. The casing 26.1 includes openings 32 arranged according to a first geometric pattern and comprises the segment 27 extending parallel to the longitudinal axis with the webs 28' and the openings 28 distanced to each other in axial direction. The casing 26.1 of this embodiment with the openings 32 arranged set-off relative to each other in rows R in wall 31.1 is shown in FIG. 5 in flipped-open position. At each side of the segment 27 extending in axial direction, a portion 26.1.1 of the casing 26.1 is shown. When combined, the two portions 26.1.1. form the hollow cylindrical tube 25.1 having, for example, a screen-like perforated casing structure.

Figure 5A:
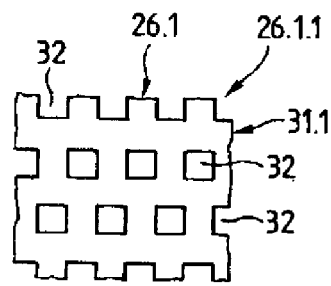
FIG. 5a is a plan view of an enlarged section of the tube wall according to FIG. 5 showing the openings in the first geometric pattern.

FIG. 5a shows an enlarged portion 26.1.1. of casing 26.1 with openings 32 in the wall 31.1 that are distanced relative to each other axially oriented and set off in rows R as well as arranged perpendicular thereto. The openings 32 as shown in FIG. 5 or FIG. 5a, are square, but they can also be circular or oval, not shown here in detail.

Figure 6:
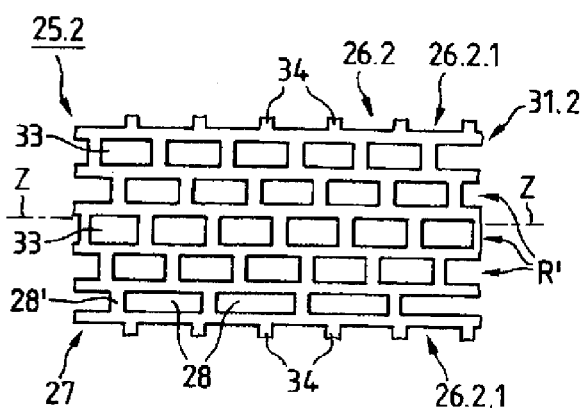
FIG. 6 is a plan view of a section of the tube showing the openings distributed in a second geometric pattern and the additional openings.

FIG. 6 shows a top view of a second embodiment of the tube 25.2 with the casing 26.2. The casing provided with openings 33 that are arranged in a second geometric pattern for example as rectangular openings 33 includes the segment 27 oriented along axis Z extending in axial direction and openings 28 arranged distanced to each other in axial direction and the webs 28' therebetween. In an opened position, at each side of the segment 27, a portion 26.2.1 of the casing 26.2 is provided with webs 34. When combined, the two portions 26.2.1. form the implant configured as a cylindrical hollow tube 25.2 with a perforated casing structure. Casing 26.2 includes a multitude of openings 33 in the wall 31.2 that are arranged distanced from each in direction of longitudinal axis Z and set off from each other in rows R'. In this variant, for example, the openings are rectangular or oval in shape and set off relative to row R' with respect to the other row R'. The two portions 26.2.1 in combined position form the tube 25.2 configured as the implant having a perforated casing structure with elongated openings.

Figure 7:
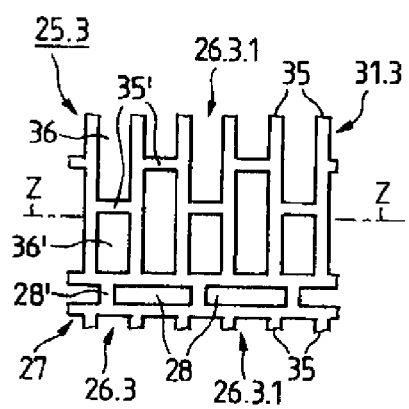
FIG. 7 is a plan view of a section of the tube showing the openings distributed in a third geometric pattern and the additional openings.

FIG. 7 shows a plan view of a third embodiment of tube 25.3 comprising the casing 26.3. The casing includes a third geometric patterns of openings 36 and 36' distributed in the wall 31.3 in a latticed pattern and includes the segment 27 oriented in axial direction and extending parallel to the longitudinal axis and the openings 28 arranged distanced from each in axial direction and the webs 28'. In opened position, at each side of the segment 27, a portion 26.3.1 is shown which each is provided with radially oriented first webs 35 and second webs 35' arranged perpendicular thereto. Between each of the circumferentially arranged first webs 35 and the second webs 35' arranged in axial direction therebetween, openings 36 and 36' are shown set off relative to each other. When combined, the two portions 26.3.1 form the implant configured as a hollow cylindrical tube 25.3 with the casing substantially configured in a latticed (grid-like) pattern.

FIG. 8 shows a perspective view of a fourth embodiment of the tube 25.4 with the segment 27 extending in direction of the longitudinal axis Z and the openings 28 arranged at a distance to each other as well as the ring parts 29 disposed at the segment 27 and distanced relative to each other. The ring parts 29 which essentially form the interior space 30 of the tube 25.4 are formed at the segment part 27 oriented in axial direction of the tube 25.4.

Figure 8A:
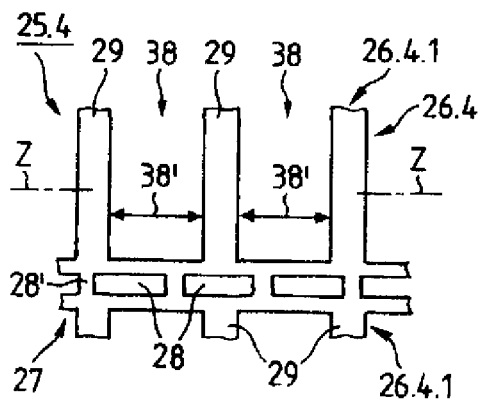
FIG. 8a is a plan view of the section of the tube according to FIG. 8 with the gaps between the ring parts and the additional openings in the segment.

FIG. 8a shows a fourth embodiment where the tube 25.4, according to FIG. 8, with the casing 26.4 in a plan view, with the axially oriented segment 27 and each of the openings 28 which are distanced from each other by webs 28' disposed therebetween. In this embodiment, the gaps 38 oriented circumferentially at the tube are each arranged with distance 38' between the single ring parts 29. The distance 38' is for example, two times to three times the width of each ring part 29. When combined, the two portions 26.4.1 with the segment 27, the ring parts 29 and the gaps 38 and openings 28 form the hollow cylindrical tube 25.4 configured as an implant. The single ring part 29 oriented parallel to each other form the substantially grid-like casing structure.

Figure 9:
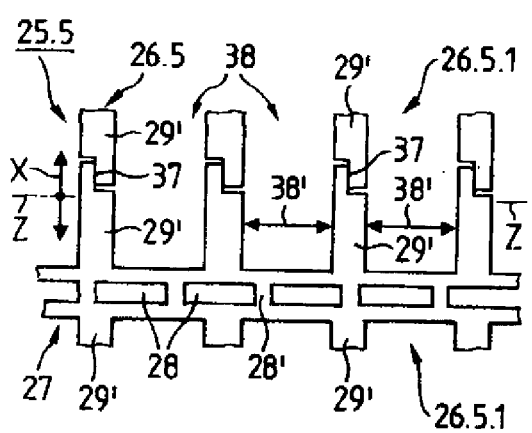
FIG. 9 is a plan view of the section of the tube according to FIG. 8a with the gaps between the ring parts as well as the additional openings, where the ring parts show a Z-shaped slit.

FIG. 9 shows a further embodiment of tube 25.5 with the casing 26.5 in a front view with the axially oriented segment 27 and the openings 28 distanced from each other with the webs 28' and the gaps 38 in axial direction distanced by distance 38' and the ring parts 29 formed at segment 27. When combined, the two portions 26.5.1 form the implant configured as a hollow cylindrical tube 25.5 with the grid-like casing structure analog to and according to FIG. 8a.

In the variant according to FIG. 9, the ring parts 29 distanced relative to each other in axial direction, at their outer circumference are each divided by a Z-shaped slot or gap 37 into two semicircular portions 29'. The two portions 29' each can spread apart relative to the longitudinal axis Z according to direction of arrow X in radial direction. In this embodiment, the distance 38' forming gaps 38 between each of the ring parts 29, is about two to three fold the breadth of each of the ring parts 29.

Figure 10:
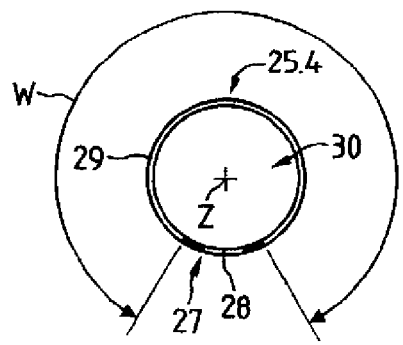
FIG. 10 is a front view and a cross section profile of the tube as shown in FIG. 8a with the additional openings.

In FIG. 10, the tube 25.4 or 25.5 provided with the ring parts 29 and the interior space 30 is shown in profiled cross section with the circular ring part 29 and the circular shaped segment 27 provided with the openings 28 oriented in axial direction. The gaps 38 arranged between the each of the ring parts 29 each have an opening angle W on the order of between 290° to 310°.

The openings shown in FIGS. 5 to 9 and configured as elongated holes disposed in segment 27, as well as the openings 33 at the tube 25.2 according to FIG. 6 each are configured as a rectangular elongated hole. In a variant not shown here, it is possible that the single opening 33, which is an elongated hole at the opposite ends is configured with a semicircular front side.

The implant configured as a hollow cylindrical tube 25.1 to 25.5 as afore-described in FIGS. 4 to 10 have an outer diameter on the order of about 0.15 mm to 0.35 mm as well as an inner diameter on the order of 0.1 mm to 0.25 mm. The openings 32, 33, 36, 36' and gaps 38 arranged in the casing of tube 25.1 to 25.5 and formed in a geometric pattern or geometric structure and the opening 28 axially oriented in the segment 27 are produced by means of a suitable micro-material treatments, preferably by means of a known laser technique, for example with an excimer laser.

At this point it should be noted that ridges or rough edges that occur when utilizing laser structured micro treatments at the tubes 25.1 to 25.5, at their surfaces or at any of the edges of each of the openings 32, 33, 36, 36' and gaps 38 (FIGS. 5, 5a, 6, 7) as well as at the ring parts 29 (FIGS. 8, 8a, 9) and at the segment 27 with the openings 28, can be removed with suitable means.

To remove projecting edges, frays or such, different micro-treatment methods are available such as for example, thermal energy machining, honing, lapping or similar, whereby ridges and also those that are at hard to reach locations can be removed with the various methods. Especially advantageous is that all edges, in particular those that occur at each of the circular ring parts 29 (FIG. 8) as well as those at the axially oriented segment 27 with a radius of about 0.025 mm to 0.2, can be smoothed off.

With the afore-described micro-treatment methods, each of the tubes 25.1 to 25.5 are produced with absolutely smoothly polished surface and smoothed edges with which insertion of the implant into the Schlemm's canal is realized without injuries or problems.

The tube 25.1 to 25.5 is for example made from biologically compatible material, for example, from polymeric material having shape and thermal or mechanical memory properties that is arc shaped and flexible, also with respect to the diameter, for insertion into the lumen 16 of the Schlemm's canal 15, which as a result of the body temperature, is returned to its original shape. Preferably, the tube 25.1 to 25.5 is produced from gold or nitinol and provided with a heparin coating.

Insertion of one of the afore-described implants configured as a tube 25.1 to 25.5 into the lumen 16 of the Schlemm's canal 15 is carried out in that the Schlemm's' canal is first carefully circumferentially dilated with the known method of canaloplasty by means of which a flexible micro-catheter and, at the same time or subsequently, a highly molecular viscous-elastic medium is injected. After successful mechanical dilation, the tube, as for example schematically shown in FIGS. 3 and 3a is inserted into the dilated Schlemm's canal 15. With the afore-described tubes 25.1 to 25.5, as schematically shown in each of the figures, the lumen 16 of the circular Schlemm's canal 15 is kept permanently open and the trans-trabecular drainage of the aqueous humor thereby realized.

While the invention has been illustrated and described as embodied in an implant for drainage of aqueous humor from the Schlemm's canal, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A one-piece implant for the treatment of glaucoma in an eye by drainage of the transtrabecular aqueous humor of Schlemm's canal comprising:
   a flexible, bendable tube which extends in an axial direction, the tube having a circular cross section; the tube further comprising:
   (1) an outer wall having a plurality of openings spaced apart in the axial direction and in a circumferential direction; the plurality of openings comprising a plurality of first openings and a plurality of second openings;
   (2) the plurality of first openings distributed at the outer wall of the tube;
   (3) an axially extending segment comprising the plurality of second openings, the second openings arranged distanced from each other in the axial direction, and configured as rectangular elongated holes separated by webs;
   (4) a plurality of circular arc shaped ring parts distanced from each other in the axial direction such that the first openings are formed therebetween, and wherein the first openings extend in the circumferential direction from one side of the segment to an opposite side of the segment, each of said first openings having an angle of 290° to 310° around the circumference of the tube.

2. The implant of claim 1, wherein each ring part is at a side opposite the segment, and divided by a slot into two ring portions, wherein each slot is arranged in the axial direction of the tube such that the ring portions can be spread apart relative to one another and can return to their original shape.

3. The implant of claim 2, wherein each slot is Z-shaped.

4. The implant of claim 1, wherein the tube is made from biologically compatible material.

5. The implant of claim 4, wherein the tube is made from polymeric material having thermal- or mechanic shape memory and is provided with a heparin-coating.

6. The implant of claim 4, wherein the tube is made from gold.

7. The implant of claim 4, wherein the tube is made from nitinol.

8. The implant of claim 1, wherein the tube is bendable into a circular arc shape and flexible relative to the cross section of the tube.

9. The implant according to claim 1, wherein the first openings are arranged in a geometric pattern in the wall of tube and the segment provided with the second openings and the circular arc shaped ring parts are produced by means of microlaser treatment.

10. The implant according to claim 9, wherein edges that resulted from the laser treatment at the tube are rounded with a radius of 0.025 mm to 0.2 mm.

11. The implant according to claim 10, wherein the edges of the circular arc shaped ring part are rounded with a radius of 0.025 mm to 0.2 mm.

12. The implant according to claim 1, wherein the first openings are arranged in a geometric pattern in the wall of tube and the segment provided with the second openings and the circular arc shaped ring parts are produced by means of an excimer laser.

* * * * *